(12) United States Patent
Hirota (10) Patent No.: US 10,098,547 B2
(45) Date of Patent: Oct. 16, 2018

(54) PHOTOACOUSTIC MEASUREMENT DEVICE, PHOTOACOUSTIC MEASUREMENT METHOD, AND PROBE CONTACT DETERMINATION METHOD

(71) Applicant: FUJIFILM Corporation, Tokyo (JP)

(72) Inventor: Kazuhiro Hirota, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/816,912

(22) Filed: Aug. 3, 2015

(65) Prior Publication Data

US 2015/0335252 A1    Nov. 26, 2015

Related U.S. Application Data

(63) Continuation of application No. PCT/JP2014/056868, filed on Mar. 14, 2014.

(30) Foreign Application Priority Data

Mar. 21, 2013    (JP) ................. 2013-057641

(51) Int. Cl.
*A61B 5/00* (2006.01)

(52) U.S. Cl.
CPC .......... *A61B 5/0095* (2013.01); *A61B 5/7203* (2013.01); *A61B 5/7246* (2013.01);
(Continued)

(58) Field of Classification Search
CPC ..................................................... A61B 8/429
See application file for complete search history.

(56) References Cited

U.S. PATENT DOCUMENTS

| 2007/0015978 A1* | 1/2007 | Kanayama ........... A61B 5/0095 600/310 |
| 2013/0338478 A1 | 12/2013 | Hirota et al. |
| 2014/0018661 A1 | 1/2014 | Tsujita et al. |

FOREIGN PATENT DOCUMENTS

| JP | 2009-011593 A | 1/2009 |
| JP | 2012-187389 A | 10/2012 |

(Continued)

OTHER PUBLICATIONS

Decision to Grant a Patent received in the corresponding JP Application No. 2013-057641 dated Mar. 11, 2016 with an English Translation.

(Continued)

*Primary Examiner* — Joseph M Santos Rodriguez
(74) *Attorney, Agent, or Firm* — Birch, Stewart, Kolasch & Birch, LLP (57) ABSTRACT

A photoacoustic measurement device 10 includes a probe 11 having a light emitting unit that emits measurement light L and a plurality of acoustic wave detection elements, a determination unit 28 that determines whether a state between the probe 11 and a subject M is a contact state or a non-contact state, and a light intensity control unit (for example, a switching control unit 36 and an intensity switching unit 37) that controls the intensity of the measurement light such that the measurement light has a first intensity or a second intensity higher than the first intensity, on the basis of the determination result of the determination unit 28. The determination unit 28 performs the determination on the basis of the status of a change in a plurality of photoacoustic signals detected by the plurality of acoustic wave detection elements.

17 Claims, 8 Drawing Sheets

(52) U.S. Cl.
CPC .......... *A61B 5/6843* (2013.01); *A61B 5/6844* (2013.01); *A61B 2562/04* (2013.01)

(56) References Cited

FOREIGN PATENT DOCUMENTS

| | | | |
|---|---|---|---|
| JP | 2012-187394 A | 10/2012 | |
| JP | 2012-205886 A | 10/2012 | |
| JP | WO 2012140865 A1 * | 10/2012 | ........... A61B 5/0095 |
| JP | WO 2012150655 A1 * | 11/2012 | ........... A61B 5/0095 |
| JP | 2013-103064 A | 5/2013 | |
| WO | WO 2012/114730 A1 | 8/2012 | |
| WO | WO 2012/124341 A1 | 9/2012 | |

OTHER PUBLICATIONS

International Search Report issued in PCT/JP2014/056868 dated Apr. 22, 2014.
Written Opinion of the International Searching Authority issued in PCT/JP2014/056868 dated Apr. 22, 2014.

* cited by examiner

PHOTOACOUSTIC MEASUREMENT DEVICE, PHOTOACOUSTIC MEASUREMENT METHOD, AND PROBE CONTACT DETERMINATION METHOD

CROSS-REFERENCE TO RELATED APPLICATIONS

This application is a Continuation of PCT International Application No. PCT/JP2014/056868 filed on Mar. 14, 2014, which claims priority under 35 U.S.C. § 119(a) to Japanese Patent Application No. 2013-057641 filed on Mar. 21, 2013. Each of the above application(s) is hereby expressly incorporated by reference, in its entirety, into the present application.

BACKGROUND OF THE INVENTION

1. Field of the Invention

The present invention relates to a photoacoustic measurement device for performing measurement in a subject on the basis of a photoacoustic signal generated in the subject. In addition, the invention relates to a photoacoustic measurement method and a probe contact determination method that are performed using the photoacoustic measurement device.

2. Description of the Related Art

In recent years, a non-invasive measurement method using a photoacoustic effect has drawn attention. This measurement method irradiates a subject with pulsed light having a predetermined wavelength (for example, the wavelength range of visible light, near-infrared light, or middle infrared light), detects photoacoustic waves, which are elastic waves generated when an absorbing material in the subject absorbs the energy of the pulsed light, and quantitatively measures the concentration of the absorbing material. Examples of the absorbing material in the subject include glucose or hemoglobin in the blood. In addition, a technique that detects the photoacoustic waves and generates a photoacoustic image on the basis of the detected signal is referred to as photoacoustic imaging (PAI) or photoacoustic tomography (PAT).

In the photoacoustic measurement, the photoacoustic waves are detected by a probe including a light emitting unit, such as an optical fiber, and an acoustic wave detection element, such as a piezoelectric element. However, in the case where the probe is used, a handling performance is improved, but measurement light is emitted in an unintended direction.

In order to solve this problem, for example, JP2009-011593A, JP2012-187389A, JP2012-205886A, and JP2012-187394A disclose a method which determines whether a probe comes into contact with a subject and increases or decreases the intensity of measurement light on the basis of the determination result.

Specifically, JP2009-011593A discloses a method which extracts two predetermined peaks from a signal detected by a piezoelectric sensor, performs contact determination on the basis of information indicating the position of the peaks, and increases the intensity of the measurement light on the basis of the determination result. In addition, JP2012-187389A or JP2012-205886A discloses a method which performs contact determination on the basis of an ultrasonic image that is previously acquired and emits the measurement light on the basis of the determination result. JP2012-187394A discloses a method which performs contact determination on the basis of the distance measured by distance measuring laser light and emits the measurement light on the basis of the determination result.

SUMMARY OF THE INVENTION

However, in the method disclosed in JP2009-011593A, it is assumed that the amount of glucose or hemoglobin is measured from the photoacoustic signal detected by a single acoustic wave detection element (piezoelectric sensor). Therefore, this method is not necessarily suitable for photoacoustic measurement using a probe having a plurality of acoustic wave detection elements. For example, in the case in which a probe having a plurality of acoustic wave detection elements is used, when one acoustic wave detection element detects a signal, most of a contact portion (or a detection surface) of the probe may be exposed.

In addition, it is preferable to perform contact determination using a simple method in order to improve a frame rate or to reduce the size of the probe.

The invention has been made in view of the above-mentioned problems and an object of the invention is to provide a photoacoustic measurement device, a photoacoustic measurement method, and a probe contact determination method which can perform contact determination using a simpler method in photoacoustic measurement using a probe having a plurality of acoustic wave detection elements.

In order to solve the above-mentioned problems, according to an aspect of the invention, there is provided a photoacoustic measurement device including: a probe having a light emitting unit that emits measurement light and a plurality of acoustic wave detection elements that measure a photoacoustic signal from a subject which is caused by the emission of the measurement light; a determination unit that determines whether a state between the probe and the subject is a contact state or a non-contact state; and a light intensity control unit that controls the intensity of the measurement light such that the measurement light has a first intensity when the determination unit determines that the state between the probe and the subject is the non-contact state and controls the intensity of the measurement light such that the measurement light has a second intensity higher than the first intensity when the determination unit determines that the state between the probe and the subject is the contact state. The determination unit performs the determination on the basis of a status of a change in a plurality of photoacoustic signals detected by the plurality of acoustic wave detection elements.

In the photoacoustic measurement device according to the above-mentioned aspect of the invention, the determination unit may calculate the number of acoustic wave detection elements which detect the plurality of photoacoustic signals on the basis of the plurality of photoacoustic signals, determine a change in the number of acoustic wave detection elements as the change in the plurality of photoacoustic signals, compare the number of acoustic wave detection elements with a threshold number of acoustic wave detection elements, and perform the determination on the basis of the comparison result.

In the case in which the change in the number of acoustic wave detection elements is determined as the change in the plurality of photoacoustic signals, it is preferable that the threshold number of acoustic wave detection elements when a change from the contact state to the non-contact state is determined is less than the threshold number of acoustic wave detection elements when a change from the non-contact state to the contact state is determined. Alternatively, the threshold number of acoustic wave detection elements when the change from the contact state to the non-contact state is determined may be equal to the threshold number of acoustic wave detection elements when the change from the non-contact state to the contact state is determined.

In the case in which the change in the number of acoustic wave detection elements is determined as the change in the plurality of photoacoustic signals, the determination unit may count the number of only specific acoustic wave detection elements among the plurality of acoustic wave detection elements. In this case, it is preferable that the specific acoustic wave detection elements are acoustic wave detection elements which are consecutively arranged in the vicinity of the center of an array of the plurality of acoustic wave detection elements.

Alternatively, in the photoacoustic measurement device according to the above-mentioned aspect of the invention, the determination unit may detect the appearance or disappearance of an absorber region indicating an absorber in the subject and an artifact region indicating an artifact caused by the emission of the measurement light in a photoacoustic image which is generated on the basis of the plurality of photoacoustic signals, determine the appearance or disappearance of the absorber region and the artifact region as the change in the plurality of photoacoustic signals, and perform the determination on the basis of a combination of the appearance and disappearance of the absorber region and the artifact region.

In the photoacoustic measurement device according to the above-mentioned aspect of the invention, in the case in which the appearance or disappearance of the absorber region and the artifact region is determined as the change in the plurality of photoacoustic signals, during the determination of the change from the contact state to the non-contact state, when the artifact region is detected in the photoacoustic image, the determination unit may determine that the state between the probe and the subject has changed from the contact state to the non-contact state. In addition, during the determination of the change from the non-contact state to the contact state, when the artifact region is detected in the photoacoustic image and the absorber region is detected after the artifact region is detected, the determination unit may determine that the state between the probe and the subject has changed from the non-contact state to the contact state.

According to another aspect of the invention, there is provided a photoacoustic measurement method including: using the photoacoustic measurement device; using the probe having the light emitting unit that emits measurement light and the plurality of acoustic wave detection elements; determining whether a state between the probe and the subject is the contact state or the non-contact state on the basis of the status of a change in the plurality of photoacoustic signals detected by the plurality of acoustic wave detection elements; controlling the intensity of the measurement light such that the measurement light has the first intensity when it is determined that the state between the probe and the subject is the non-contact state and controlling the intensity of the measurement light such that the measurement light has the second intensity higher than the first intensity when it is determined that the state between the probe and the subject is the contact state, thereby measuring the photoacoustic signals from the subject.

In the photoacoustic measurement method according to the above-mentioned aspect of the invention, the number of acoustic wave detection elements which detect the plurality of photoacoustic signals may be calculated on the basis of the plurality of photoacoustic signals. A change in the number of acoustic wave detection elements may be determined as the change in the plurality of photoacoustic signals. The number of acoustic wave detection elements may be compared with a threshold number of acoustic wave detection elements and the determination may be performed on the basis of the comparison result.

In the photoacoustic measurement method according to the above-mentioned aspect of the invention, in the case in which the change in the number of acoustic wave detection elements is determined as the change in the plurality of photoacoustic signals, it is preferable that the threshold number of acoustic wave detection elements when a change from the contact state to the non-contact state is determined is less than the threshold number of acoustic wave detection elements when a change from the non-contact state to the contact state is determined.

In the photoacoustic measurement method according to the above-mentioned aspect of the invention, in the case in which the change in the number of acoustic wave detection elements is determined as the change in the plurality of photoacoustic signals, the number of only specific acoustic wave detection elements among the plurality of acoustic wave detection elements may be counted.

Alternatively, in the photoacoustic measurement method according to the above-mentioned aspect of the invention, the appearance or disappearance of an absorber region indicating an absorber in the subject and an artifact region indicating an artifact caused by the emission of the measurement light may be detected in a photoacoustic image which is generated on the basis of the plurality of photoacoustic signals. The appearance or disappearance of the absorber region and the artifact region may be determined as the change in the plurality of photoacoustic signals. The determination may be performed on the basis of a combination of the appearance and disappearance of the absorber region and the artifact region.

In the photoacoustic measurement method according to the above-mentioned aspect of the invention, in the case in which the appearance or disappearance of the absorber region and the artifact region is determined as the change in the plurality of photoacoustic signals, during the determination of the change from the contact state to the non-contact state, when the artifact region is detected in the photoacoustic image, it may be determined that the state between the probe and the subject has changed from the contact state to the non-contact state. In addition, during the determination of the change from the non-contact state to the contact state, when the artifact region is detected in the photoacoustic image and the absorber region is detected after the artifact region is detected, it may be determined that the state between the probe and the subject has changed from the non-contact state to the contact state.

According to still another aspect of the invention, there is provided a probe contact determination method including: using the photoacoustic measurement device; using the probe having the light emitting unit that emits measurement light and the plurality of acoustic wave detection elements; and determining whether a state between the probe and the subject is the contact state or the non-contact state on the basis of the status of a change in the plurality of photoacoustic signals detected by the plurality of acoustic wave detection elements.

In the probe contact determination method according to the above-mentioned aspect of the invention, the number of acoustic wave detection elements which detect the plurality of photoacoustic signals may be calculated on the basis of the plurality of photoacoustic signals. A change in the number of acoustic wave detection elements may be determined as the change in the plurality of photoacoustic signals. The number of acoustic wave detection elements may be compared with a threshold number of acoustic wave detection elements and the determination may be performed on the basis of the comparison result.

Alternatively, in the probe contact determination method according to the above-mentioned aspect of the invention, the appearance or disappearance of an absorber region indicating an absorber in the subject and an artifact region indicating an artifact caused by the emission of the measurement light may be detected in a photoacoustic image which is generated on the basis of the plurality of photoacoustic signals. The appearance or disappearance of the absorber region and the artifact region may be determined as the change in the plurality of photoacoustic signals. The determination may be performed on the basis of a combination of the appearance and disappearance of the absorber region and the artifact region.

In the probe contact determination method according to the above-mentioned aspect of the invention, in the case in which the appearance or disappearance of the absorber region and the artifact region is determined as the change in the plurality of photoacoustic signals, during the determination of the change from the contact state to the non-contact state, when the artifact region is detected in the photoacoustic image, it may be determined that the state between the probe and the subject has changed from the contact state to the non-contact state.

The photoacoustic measurement device according to the invention includes the determination unit that performs contact determination on the basis of the status of a change in a plurality of photoacoustic signals detected by a plurality of acoustic wave detection elements. Therefore, it is possible to more accurately check the contact state between the probe and the subject than in the related art. In addition, according to the invention, it is not necessary to provide other contact detection components (for example, a contact detection sensor or length measurement means). As a result, in photoacoustic measurement which uses a probe including a plurality of acoustic wave detection elements, it is possible to perform the contact determination using a simpler method than in the related art.

The photoacoustic measurement method and the probe contact determination method according to the invention perform contact determination on the basis of the status of a change in a plurality of photoacoustic signals detected by a plurality of acoustic wave detection elements. Therefore, it is possible to more accurately check the contact state between the probe and the subject than in the related art. As a result, similarly to the above, in photoacoustic measurement which uses a probe including a plurality of acoustic wave detection elements, it is possible to perform the contact determination using a simpler method than in the related art.

DESCRIPTION OF THE PREFERRED EMBODIMENTS

Hereinafter, embodiments of the invention will be described with reference to the drawings. However, the invention is not limited to the embodiments. For ease of viewing, for example, the scale of each component in the drawings is different from the actual scale.

First Embodiment

Figure 1:
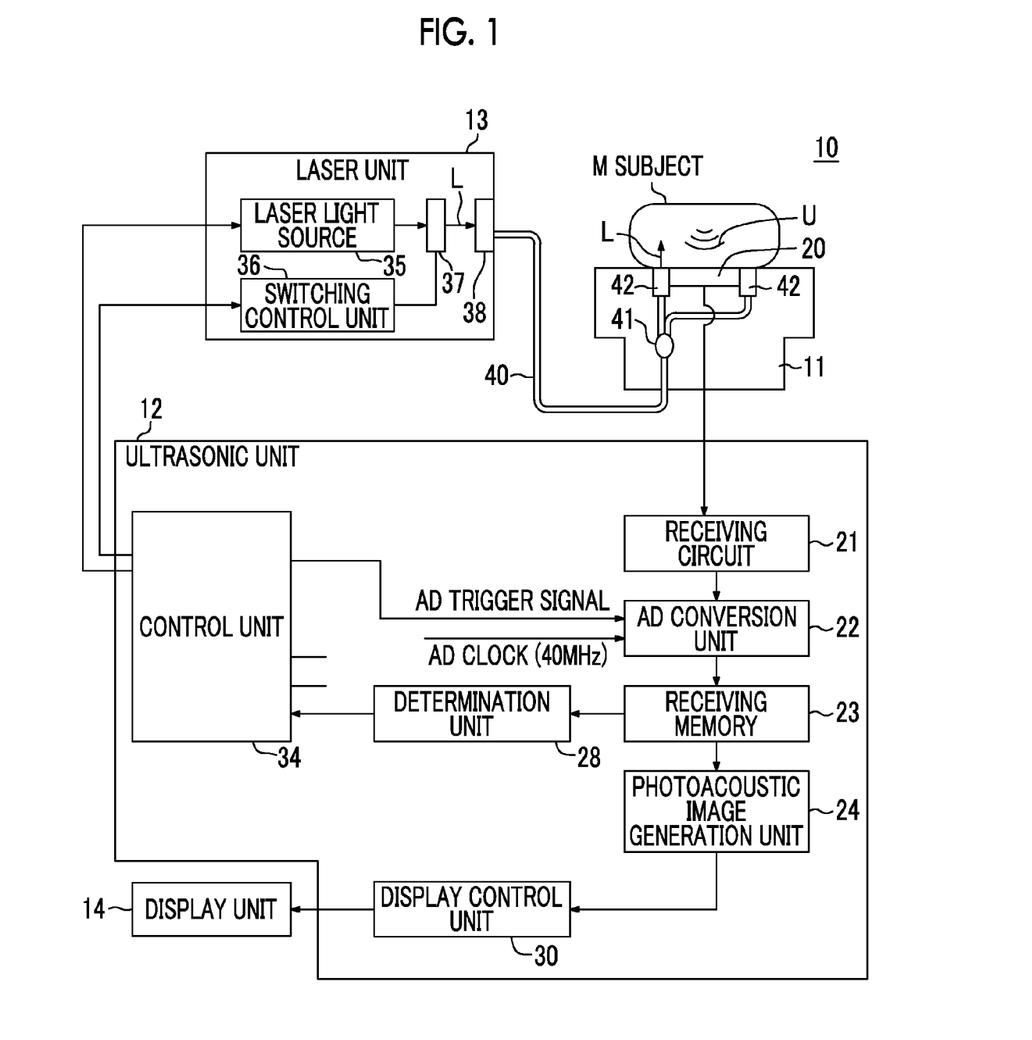
FIG. 1 is a conceptual diagram illustrating the structure of a photoacoustic measurement device according to a first embodiment.
Figure 2A:
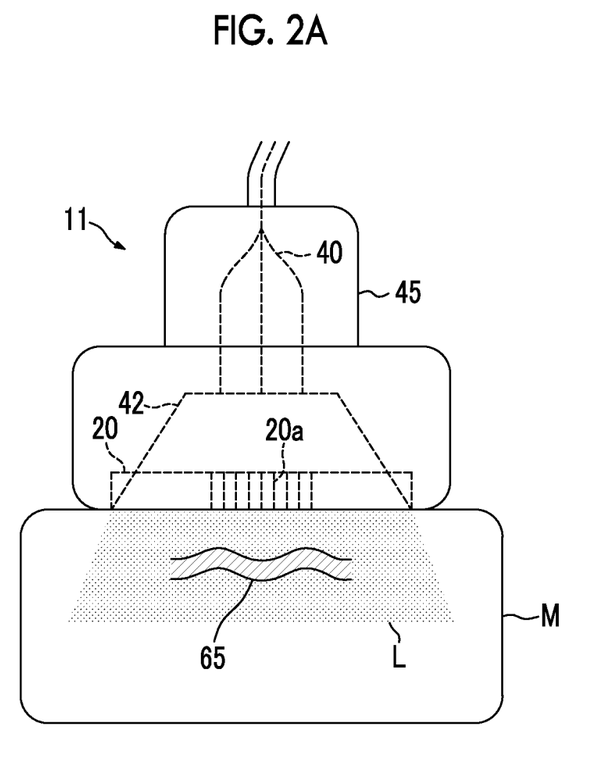
FIG. 2A is a front view schematically illustrating the structure of a probe and FIG. 2B is a side view schematically illustrating the structure of the probe.
Figure 2B:
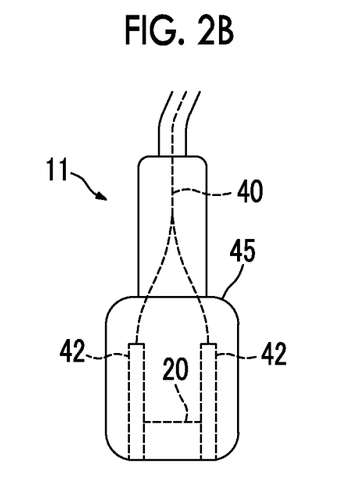

First, a first embodiment of a photoacoustic measurement device, a photoacoustic measurement method, and a probe contact determination method according to the invention will be described. FIG. 1 is a conceptual diagram illustrating the structure of the photoacoustic measurement device according to the first embodiment. FIG. 2A is a front view schematically illustrating the structure of a probe. FIG. 2B is a side view schematically illustrating the structure of the probe.

A photoacoustic measurement device 10 according to this embodiment has, for example, a photoacoustic image generation function of generating a photoacoustic image on the basis of a photoacoustic signal. Specifically, as illustrated in FIG. 1, the photoacoustic measurement device 10 according to this embodiment includes an ultrasonic probe (probe) 11, an ultrasonic unit 12, a laser unit 13, and a display unit 14.

<Probe>

The probe 11 irradiates a subject with ultrasonic waves or detects acoustic waves U which are propagated through a subject M. That is, the probe 11 can emit (transmit) ultrasonic waves to the subject M and detect (receive) ultrasonic waves (reflected acoustic waves) reflected from the subject M. In addition, the probe 11 can detect photoacoustic waves which are generated in the subject M by the absorption of laser light by an absorber 65 in the subject M. In the specification, the "acoustic waves" include ultrasonic waves and photoacoustic waves. Here, the "ultrasonic wave" means an elastic wave which is transmitted by the probe and the "photoacoustic wave" means an elastic wave which is generated in the subject M by a photoacoustic effect obtained by irradiation with measurement light. Examples of the absorber 65 include a blood vessel and a metal member.

For example, as illustrated in FIG. 1 and FIGS. 2A and 2B, the probe 11 according to this embodiment includes a transducer array 20, an optical fiber 40, a light guide plate 42, and a housing 45 that contains these components. The transducer array 20 is constituted of, for example, a plurality of ultrasonic transducers 20a (acoustic wave detection elements) that are one-dimensionally or two-dimensionally arranged. The ultrasonic transducer 20a is a piezoelectric element constituted of a polymer film, such as a piezoelectric ceramic film or a polyvinylidene fluoride (PVDF) film. The ultrasonic transducer 20a has a function of converting a received signal into an electric signal when the acoustic wave U is received. The electric signal is output to a receiving circuit 21 which will be described below. The probe 11 is selected from, for example, a sector scanning type, a linear scanning type, and a convex scanning type according to a part to be imaged. In addition, an acoustic matching member, such as an acoustic lens, may be provided on a detection surface (a contact portion of the probe 11) of the transducer array 20 in order to more effectively detect the acoustic waves, if necessary.

The optical fiber 40 guides laser light L which is emitted from the laser unit 13 to the light guide plate 42. The optical fiber 40 is not particularly limited. However, a known fiber, such as a quartz fiber, can be used. For example, in this embodiment, the laser light L is guided from the laser unit 13 into the probe 11 by one optical fiber, is branched into a plurality of light components by a branching coupler 41 in the probe 11, and is then guided to two light guide plates 42 which will be described below. The laser light L is not necessarily guided by one optical fiber. A fiber bundle may be used.

The light guide plate 42 is, for example, a plate which is obtained by performing special processing on the surface of an acrylic plate or a quartz plate and in which light incident on one end surface is uniformly emitted from the other end surface. In this embodiment, the light guide plate 42 corresponds to a light emitting unit according to the invention. As illustrated in FIGS. 2A and 2B, in this embodiment, two light guide plates 42 are arranged on both sides of the transducer array 20 in the elevation direction (a direction that is perpendicular to the array direction of the transducer array and is parallel to the detection surface) such that the transducer array 20 is interposed between the light guide plates 42. The optical fiber 40 and the light guide plate 42 are optically coupled to each other.

As illustrated in FIGS. 2A and 2B, a portion of the light guide plate 42 which is coupled to the optical fiber 40 has, for example, a tapered shape. Therefore, it is possible to effectively expand the irradiation range of measurement light. In addition, it is preferable that the portion of the light guide plate 42 which is coupled to the optical fiber 40 is made of a glass material in order to avoid damage due to optical energy. The other portion of the light guide plate 42 is made of a resin material such as acryl.

The laser light L guided by the optical fiber 40 is incident on the light guide plate 42 and is then emitted from the opposite end to the subject M. A mechanism (for example, a resin including scattering particles) for scattering light or a mechanism (for example, a cutout for refracting light) for guiding light so as to travel to the transducer array 20 may be provided at the leading end of the light guide plate 42 such that the subject M can be irradiated with the laser light L in a wide range.

When the probe 11 is formed in the above-mentioned structure, it is possible to accurately generate an ultrasonic image and a photoacoustic image as a reflected acoustic image in the same imaging range. According to this structure, in some cases, a complicated positioning process for the ultrasonic image and the photoacoustic image is not required.

<Laser Unit>

The laser unit 13 is a light source unit that emits the laser light L to be radiated to the subject M as measurement light. When the subject M absorbs the laser light, photoacoustic waves are generated in the subject M. The laser light emitted from the laser unit 13 is guided to the leading end of the probe 11 by light guide means, such as the optical fiber 40, and is then emitted from the probe 11 to the subject M.

The laser unit 13 according to this embodiment includes, for example, a laser light source 35, such as a Q-switch alexandrite laser, a switching control unit 36 that increases or decreases the intensity (or amount) of the laser light L emitted from the laser light source 35 using an intensity switching unit 37, and a connection unit 38 that connects the laser light L whose intensity has been adjusted to the optical fiber 40. The switching control unit 36 and the intensity switching unit 37 correspond to a light intensity control unit according to the invention.

The intensity switching unit 37 is, for example, a neutral density (ND) filter. In this case, the intensity of the laser light L is adjusted according to whether the ND filter is provided. The switching control unit 36 controls the intensity switching unit 37 on the basis of the determination result of a contact by a determination unit 28, which will be described below (for example, arranges the ND filter on the optical path of the laser light L or retreats the ND filter from the optical path of the laser light L) to change the intensity of the laser light L. Specifically, when it is determined that the probe 11 does not come into contact with the subject M, the switching control unit 36 arranges, for example, the ND filter on the optical path of the laser light L and controls the intensity of the laser light L such that the laser light L has a first intensity. On the other hand, when it is determined that the probe 11 comes into contact with the subject M, the switching control unit 36 retreats, for example, the ND filter from the optical path of the laser light L and controls the intensity of the laser light L such that the laser light L has a second intensity higher than the first intensity. For example, the second intensity is a light intensity required to measure desired photoacoustic waves. The first intensity is suitable for the safety standard for the laser light. For example, in the case where laser light with a wavelength of 756 nm is used, the rough standard for the first intensity as the amount of energy which is incident on a region with a diameter of 7 mm at a position that is 10 cm away from the light source is 84 µJ in order to reduce a light intensity to a class 3R level and is 16 µJ in order to reduce a light intensity to a class 1 level.

When a trigger control circuit (not illustrated) in the control unit 34 outputs a light trigger signal, the laser unit 13 turns on a flash lamp and excites the laser light source 35. In this embodiment, it is preferable that the laser unit 13 outputs pulsed light with a pulse width of 1 nsec to 100 nsec as the laser light. The wavelength of the laser light is appropriately determined by the light absorption characteristics of the absorber in the subject to be measured. The optical absorption characteristics of hemoglobin in a living body vary depending on the state of the hemoglobin (for example, oxygenated hemoglobin, deoxygenated hemoglobin, and met-hemoglobin). In general, hemoglobin absorbs light with a wavelength of 360 nm to 1000 nm. Therefore, in the case where hemoglobin in the living body is measured, it is preferable that the wavelength of the laser light is in the range of about 600 nm to 1000 nm in which the absorption of laser light by other biological materials is relatively small. In addition, the wavelength of the laser light is preferably in the range of 700 nm to 1000 nm and more preferably in a near-infrared wavelength range (700 nm to 850 nm) in order to emit the laser light to a deep part of the subject.

In addition, light sources, such as a semiconductor laser (LD) that generates a component with a specific wavelength or monochromatic light including the component, other solid state lasers, and a gas laser, may be used as the laser light source 35.

<Ultrasonic Unit>

The ultrasonic unit 12 according to this embodiment includes a receiving circuit 21, an AD conversion unit 22, a receiving memory 23, a photoacoustic image generation unit 24, a determination unit 28, a display control unit 30, and a control unit 34.

The control unit 34 controls each unit of the photoacoustic measurement device 10 and includes, for example, a trigger control circuit in this embodiment. The trigger control circuit transmits a light trigger signal to the laser unit 13, for example, when the photoacoustic measurement device starts. Then, in the laser unit 13, the flash lamp is turned on and a laser rod starts to be excited. Then, the excited state of the laser rod is maintained and the laser unit 13 can output laser light.

Then, the control unit 34 transmits a Qsw trigger signal from the trigger control circuit to the laser unit 13. That is, the control unit 34 controls the output time of laser light from the laser unit 13 using the Qsw trigger signal. For example, the control unit 34 can be configured such that the transmission of the Qsw trigger signal starts when a predetermined switch provided in the probe 11 is pushed. According to this structure, the position of the probe 11 when the switch is pushed can be determined as a probe scanning start point. In addition, when the control unit 34 is configured such that the transmission of the Qsw trigger signal ends at the time of the next push of the switch, the position of the probe 11 when the switch is pushed can be determined as a probe scanning end point.

In this embodiment, the control unit 34 transmits a sampling trigger signal to the AD conversion unit 22 at the same time as the Qsw trigger signal is transmitted. The sampling trigger signal is used to start the sampling of the photoacoustic signal in the AD conversion unit 22. As such, when the sampling trigger signal is transmitted as the same time as the Qsw trigger signal, it is possible to sample the photoacoustic signal in synchronization with the output of the laser light.

The receiving circuit 21 receives the photoacoustic signal detected by the probe 11. The photoacoustic signal received by the receiving circuit 21 is transmitted to the AD conversion unit 22.

The AD conversion unit 22 is sampling means. When receiving the sampling trigger signal transmitted from the control unit 34, the AD conversion unit 22 samples the photoacoustic signal received by the receiving circuit 21 and converts the photoacoustic signal into a digital signal. The AD conversion unit 22 samples the received signal with a predetermined sampling period on the basis of, for example, an AD clock signal with a predetermined frequency which is input from the outside.

The receiving memory 23 stores the photoacoustic signal sampled by the AD conversion unit 22. Then, the receiving memory 23 outputs the photoacoustic signal detected by the probe 11 to the photoacoustic image generation unit 24.

The photoacoustic image generation unit 24 reconstructs the photoacoustic signal data output from the receiving memory 23 and generates a photoacoustic image. Specifically, the photoacoustic image generation unit 24 adds signal data from each ultrasonic transducer 20a with a delay time corresponding to the position of each ultrasonic transducer 20a to generate signal data corresponding to one line (delay and sum method). The photoacoustic image generation unit 24 may reconstruct the photoacoustic signal using a Fourier transform method, instead of the delay and sum method. The reconstructed data is subjected to signal processing, such as a detection process and a logarithmic conversion process, and is constructed as, for example, a tomographic image.

The display control unit 30 displays the photoacoustic image on the display unit 14, such as a display device, on the basis of the photoacoustic image data output from the photoacoustic image generation unit 24. For example, when a plurality of two-dimensional photoacoustic images are acquired by the probe 11 including a two-dimensional transducer array or probe scanning, the display control unit 30 may create volume data on the basis of the photoacoustic images and display a composite image as a three-dimensional image on the display unit 14.

The determination unit 28 determines whether or not the probe 11 comes into contact with the subject M on the basis of a status of a change in the plurality of photoacoustic signals detected by the transducer array 20 (that is, a plurality of ultrasonic transducers). The content of the photoacoustic signal detected by the transducer array 20 (the shape of the photoacoustic signal, such as the intensity of the photoacoustic signal and the width of a peak, and the current detection position of the signal) varies depending on the distance between the probe 11 and the subject M or a contact method. Then, the determination unit 28 performs the contact determination on the basis of the status of a change in the plurality of photoacoustic signals.

Specifically, for example, the determination unit 28 can calculate the number of ultrasonic transducers 20a which detect the plurality of photoacoustic signals on the basis of the plurality of photoacoustic signals and determine a change in the number of ultrasonic transducers 20a as the change in the plurality of photoacoustic signals. Then, the determination unit 28 can compare the number of ultrasonic transducers with a threshold number of ultrasonic transducers and perform the above-mentioned determination on the basis of the comparison result. In the case where the change in the number of ultrasonic transducers is determined as the change in the plurality of photoacoustic signals, the photoacoustic signal particularly means a photoacoustic signal from the absorber in the subject M. In addition, the threshold number of ultrasonic transducers means the minimum number of ultrasonic transducers used to determine the contact state. For example, in a case in which the standard that, when the number of ultrasonic transducers is equal to or greater than N, the probe 11 comes into contact with the subject M (the threshold number of ultrasonic transducers=N) is set, the determination unit 28 determines that the state between the probe 11 and the subject M has changed from a non-contact state to a contact state when the number of ultrasonic transducers changes from N−1 to N and determines that the state has changed from the contact state to the non-contact state when the number of ultrasonic transducers changes from N to N−1. For example, when the threshold number of ultrasonic transducers is set to two or more or is set to be equal to or greater than half of the total number of ultrasonic transducers, it is possible to check in stages a contact state in which the leakage of measurement light is less than that in a contact state in which a signal is detected by only one element.

In the above description, the threshold number of ultrasonic transducers required to determine a change from the non-contact state to the contact state is equal to the threshold number of ultrasonic transducers required to determine a change from the contact state to the non-contact state. However, the invention is not limited thereto. For example, the threshold number of ultrasonic transducers required to determine the change from the contact state to the non-contact state may be set to be less than the threshold number of ultrasonic transducers required to determine the change from the non-contact state to the contact state.

Figure 3:
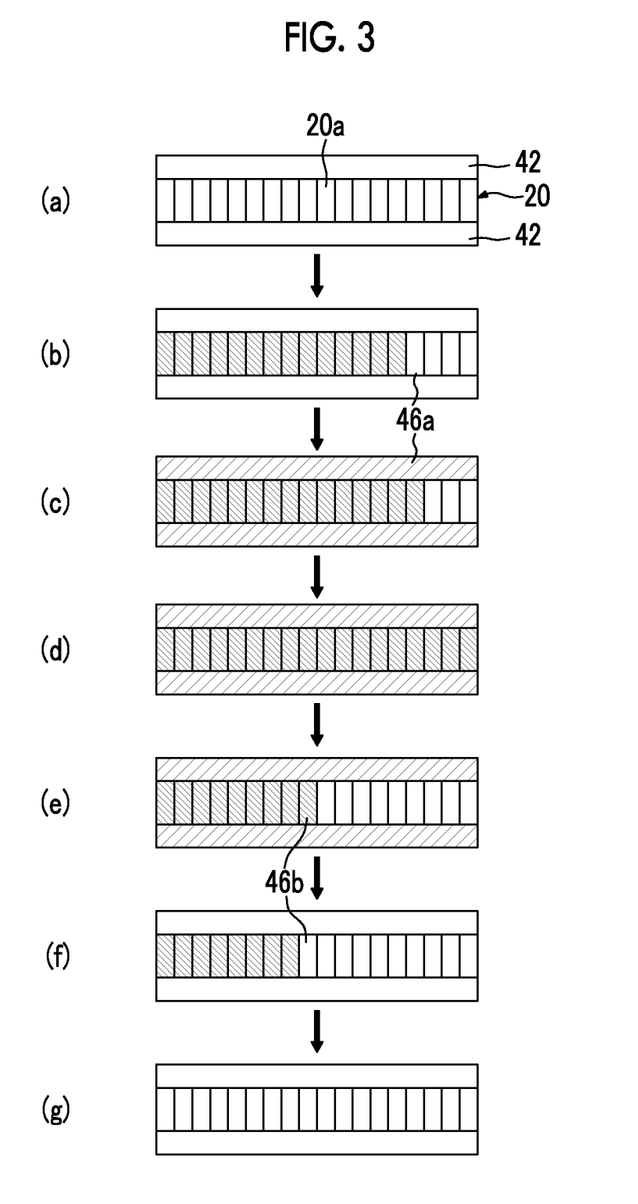
FIG. 3 is a conceptual diagram illustrating an example of contact determination based on the number of acoustic wave detection elements that detect signals (in the case where all of the detection elements are used).

FIG. 3 is a conceptual diagram illustrating an example of the contact determination. For example, FIG. 3 illustrates a state in which the transducer array 20 including eighteen ultrasonic transducers 20a is interposed between two light guide plates 42. First, when the probe is separated from the subject, no ultrasonic transducer 20a detects a photoacoustic signal ((a) of FIG. 3). When the probe starts to come into contact with the subject, the number of ultrasonic transducers 20a (a hatched portion in (b) of FIG. 3) which actually detect signals increases ((b) of FIG. 3). In addition, when the number of ultrasonic transducers 20a reaches the threshold number of elements (fifteen in FIG. 3) required to determine the change from the non-contact state to the contact state, that is, when a fifteenth ultrasonic transducer 46a from the left end detects a signal, the determination unit 28 determines that the state has changed to the contact state and the determination result is transmitted to the switching control unit 36 through the control unit 34. As a result, laser light with the second intensity is emitted from the light guide plate 42 ((c) of FIG. 3). A hatched portion of the light guide plate 42 indicates a state in which the laser light with the second intensity is emitted. Then, photoacoustic measurement is performed with the entire transducer array 20 coming into contact with the subject ((d) of FIG. 3). Then, when the probe starts to be separated from the subject after the photoacoustic measurement ends, the number of ultrasonic transducers 20a which actually detect signals decreases ((e) of FIG. 3). When the number of ultrasonic transducers 20a is less than the threshold number of elements (nine in FIG. 3) required to determine the change from the contact state to the non-contact state, that is, when a ninth ultrasonic transducer 46b from the left end does not detect a signal, the determination unit 28 determines that the state has changed to the non-contact state and the determination result is transmitted to the switching control unit 36 through the control unit 34. As a result, laser light with the first intensity is emitted from the light guide plate 42 ((f) of FIG. 3). Therefore, when the state changes from the contact state to the non-contact state, it is possible to reduce the intensity of the laser light before the probe is completely separated from the subject ((g) of FIG. 3).

In the above description, the transducer array 20 comes into contact with the subject from the end. However, the transducer array 20 may come into contact with the subject at random. The calculation of the number of ultrasonic transducers which actually detect the photoacoustic signals is equivalent to the calculation of the number of ultrasonic transducers which are not capable of detecting the photoacoustic signals in the case where the total number of ultrasonic transducers is known.

In the case where the subject is manually scanned while being contacted with the probe, a partial non-contact region between the transducer array and the subject is generated in a short time due to the influence of, for example, the shaking of the arm or the body motion of the subject. In this case, the intensity of the laser light is changed whenever a partial non-contact region is generated, which results in complicated photoacoustic measurement. Therefore, as described above, the threshold number of ultrasonic transducers required to determine the change from the contact state to the non-contact state is less than the threshold number of ultrasonic transducers required to determine the change from the non-contact state to the contact state. According to this structure, even when a few partial non-contact regions are generated after the state changes to the contact state once, it is possible to continuously perform the photoacoustic measurement without any delay.

In the above description, all of the ultrasonic transducers are used to perform the contact determination. However, the invention is not limited thereto. For example, in the case where the change in the number of ultrasonic transducers is determined as the change in the plurality of photoacoustic signals, the determination unit may count the number of only specific ultrasonic transducers (acoustic wave detection elements) among the plurality of ultrasonic transducers (acoustic wave detection elements).

Figure 4:
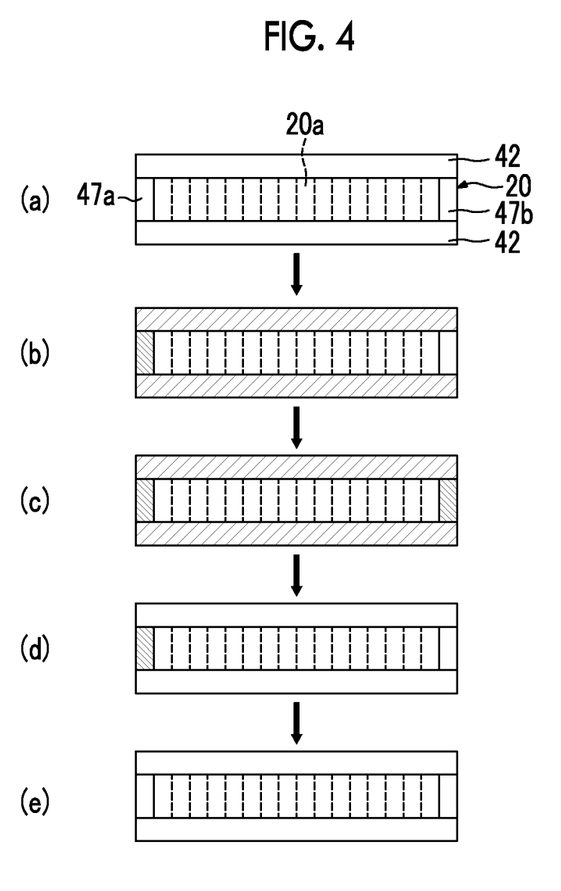
FIG. 4 is a conceptual diagram illustrating an example of the contact determination based on the number of acoustic wave detection elements that detect signals (in the case where the detection elements provided at both ends of an array are used).

FIG. 4 is a conceptual diagram illustrating an example of the contact determination. For example, in FIG. 4, two ultrasonic transducers 47a and 47b which are arranged at both ends of the transducer array 20 are used as the specific ultrasonic transducers. First, when the probe is separated from the subject, no ultrasonic transducers detect a signal ((a) of FIG. 4). Then, when the ultrasonic transducer 47a detects a signal, the determination unit 28 determines that the state has changed to the contact state and the determination result is transmitted to the switching control unit 36 through the control unit 34. As a result, laser light with the second intensity is emitted from the light guide plate 42 ((b) of FIG. 4). Then, the photoacoustic measurement is performed with the entire transducer array 20 coming into contact with the subject ((c) of FIG. 4). When the ultrasonic transducer 47b does not detect a signal after the photoacoustic measurement ends, the determination unit 28 determines that the state has changed to the non-contact state and the determination result is transmitted to the switching control unit 36 through the control unit 34. As a result, laser light with the first intensity is emitted from the light guide plate 42 ((d) of FIG. 4). Therefore, when the state changes from the contact state to the non-contact state, it is possible to reduce the intensity of the laser light before the probe is completely separated from the subject ((e) of FIG. 4).

A specific ultrasonic transducer is appropriately selected according to, for example, the type of probe or the part to be measured. For example, a group of consecutive ultrasonic transducers which are arranged in the vicinity of the center of the transducer array 20 may be used or a group of alternate ultrasonic transducers or a group of ultrasonic transducers which are arranged at intervals with two ultrasonic transducers therebetween may be used.

Figure 5:
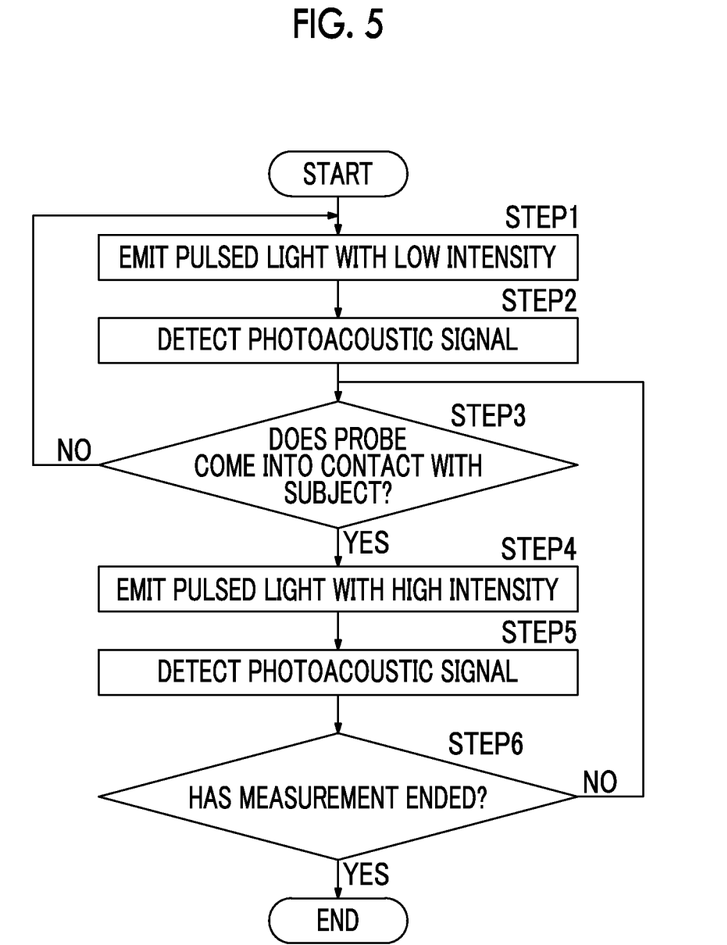
FIG. 5 is a flowchart illustrating processes of a photoacoustic measurement method according to the first embodiment.

Next, the flow of a photoacoustic measurement method and a contact determination method will be described with reference to FIG. 5. FIG. 5 is a flowchart illustrating processes of the photoacoustic measurement method according to this embodiment. First, in STEP1, since the probe 11 does not come into contact with the subject M, the laser light L with the first intensity is emitted. For example, the laser light is emitted immediately after the device 10 is turned on or in response to an appropriate button operation. Then, in STEP2, the photoacoustic signals caused by the emission of the laser light are detected. Then, in STEP3, the determination unit 28 performs contact determination on the basis of the status of a change in a plurality of detected photoacoustic signals. In the case where it is determined that the state is the contact state, the intensity of light increases to the second intensity. In STEP4, the laser light L with the second intensity is emitted. On the other hand, in the case where it is determined that the state is the non-contact state, the intensity of light is maintained and the laser light L with the first intensity is emitted again after a predetermined period of time has elapsed. In the case where the laser light L with the second intensity is emitted in STEP4, the photoacoustic signals caused by the emission of the laser light are detected in STEP5. The photoacoustic signals are used by the photoacoustic image generation unit 24 to generate the photoacoustic image. Then, in STEP6, it is determined whether the photoacoustic measurement has ended. In the case where the entire photoacoustic measurement has not ended, the contact determination is performed again on the basis of the status of a change in a plurality of photoacoustic signals which are previously detected. The contact determination may be performed whenever one pulse is generated, whenever a plurality of pulses are generated, or at a predetermined time interval.

As described above, the photoacoustic measurement device according to this embodiment has the determination unit that performs contact determination on the basis of the status of a change in a plurality of photoacoustic signals detected by a plurality of acoustic wave detection elements. Therefore, it is possible to more accurately check the contact state between the probe and the subject than in the related art. In addition, according to the invention, it is not necessary to provide other contact detection components (for example, a contact detection sensor or length measurement means). As a result, in photoacoustic measurement which uses a probe having a plurality of acoustic wave detection elements, it is possible to perform the contact determination using a simple method.

The photoacoustic measurement method and the probe contact determination method according to this embodiment perform contact determination on the basis of the status of a change in a plurality of photoacoustic signals detected by a plurality of acoustic wave detection elements. Therefore, it is possible to more accurately check the contact state between the probe and the subject than in the related art. As a result, similarly to the above, in photoacoustic measurement which uses a probe including a plurality of acoustic wave detection elements, it is possible to perform the contact determination using a simple method.

<Design Changes>

In the above description, the laser light source 35 is mainly a solid state laser. However, the invention is not limited thereto. For example, a semiconductor laser may be used as the laser light source 35. In this case, control means for controlling the driving current value of the semiconductor laser functions as the light intensity control unit according to the invention.

Second Embodiment

Next, a second embodiment of the photoacoustic measurement device, the photoacoustic measurement method, and the probe contact determination method according to the invention will be described. This embodiment differs from the first embodiment in that the appearance or disappearance of an absorber region and an artifact region in a photoacoustic image is determined as a change in a plurality of photoacoustic signals and contact determination is performed on the basis of a combination of the appearance and disappearance of the two regions. Therefore, the detailed description of the same components as those in the first embodiment will not be repeated if not particularly necessary.

The photoacoustic measurement device according to this embodiment includes an ultrasonic probe 11, an ultrasonic unit 12, a laser unit 13, and a display unit 14, similarly to the first embodiment.

Figure 6A:
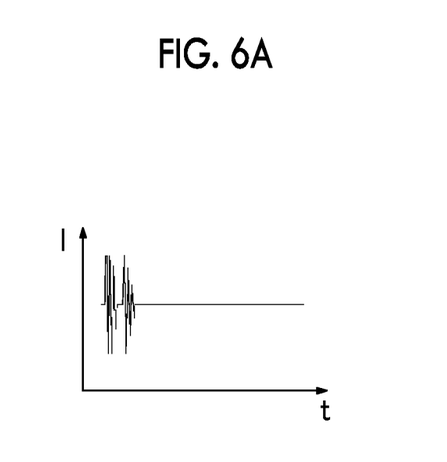
FIG. 6A is a conceptual diagram illustrating an artifact signal caused by reflected light and FIG. 6B is a conceptual diagram illustrating a photoacoustic image in which an artifact region appears.
Figure 6B:
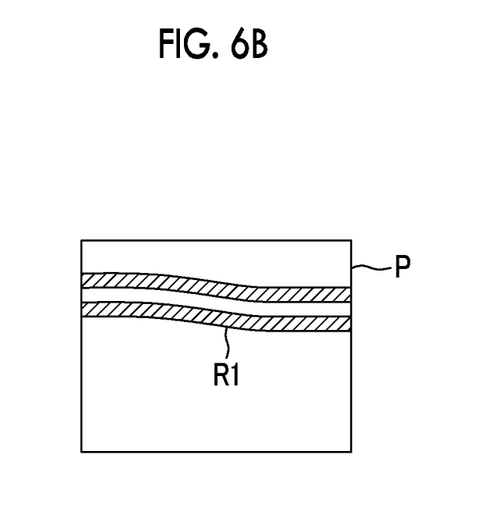

In this embodiment, a determination unit 28 determines the appearance or disappearance of the absorber region and the artifact region in the photoacoustic image as a change in a plurality of photoacoustic signals and performs contact determination on the basis of a combination of the appearance and disappearance of the two regions. The absorber region means an image region indicating an absorber in the subject and the artifact region means an image region indicating an artifact caused by the emission of measurement light. When the probe 11 is separated from a subject M, an ultrasonic transducer 20a receives light reflected from the subject M. In this case, the reflected light is absorbed by the ultrasonic transducer and the ultrasonic transducer becomes a generation source of a photoacoustic signal caused by the absorption of the reflected light. FIG. 6A is a conceptual diagram illustrating an artifact signal caused by the reflected light and FIG. 6B is a conceptual diagram illustrating a photoacoustic image P in which an artifact region R1 appears. FIG. 6A illustrates an artifact signal (right peak) which is generated from an acoustic matching member provided on the detection surface of the transducer array 20 in addition to an artifact signal (left peak) which is generated from the ultrasonic transducer. The levels of the artifact signals are saturated. When the photoacoustic signals are reconstructed into an image, for example, the photoacoustic image illustrated in FIG. 6B is obtained. In FIG. 6B, an upper strip-shaped region is an artifact region R1 which is generated from the ultrasonic transducer and a lower strip-shaped region is an artifact region R1 which is generated from the acoustic matching member.

The determination unit 28 generates photoacoustic image data on the basis of a plurality of photoacoustic signals received from a receiving memory 23 or acquires photoacoustic image data generated by a photoacoustic image generation unit 24 and detects the absorber region and the artifact region from the photoacoustic image data.

The relationship between the distance between the probe 11 and the subject M and the appearance or disappearance of the absorber region and the artifact region will be described with reference to FIG. 7. The left side of FIG. 7 is a conceptual diagram illustrating the positional relationship between the probe 11 and the subject M and the right side of FIG. 7 is a conceptual diagram illustrating photoacoustic images P which are generated on the basis of the photoacoustic signals detected in each state illustrated on the left side.

Figure 7:
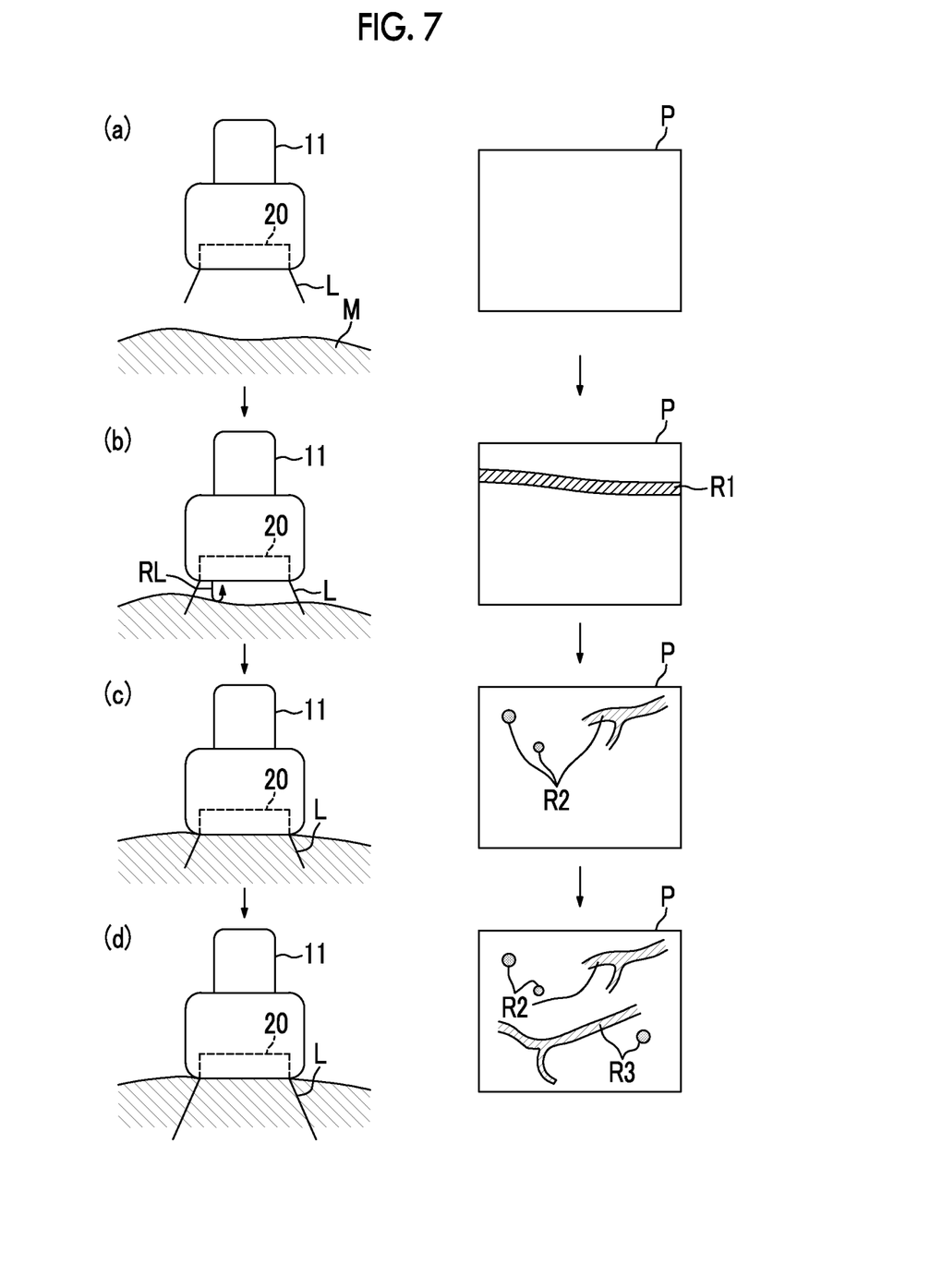
FIG. 7 is a conceptual diagram illustrating an example of contact determination based on a combination of the appearance and disappearance of an absorber region or the artifact region.

First, when the probe 11 is separated from the subject M, no artifact signal is detected since the intensity of reflected light RL of laser light L is low ((a) of FIG. 7). Most of the laser light L is reflected from the surface of the subject M and a sufficient amount of light does not reach the inside of the subject. As a result, the photoacoustic signal from the absorber is hardly detected. When the probe 11 approaches the subject M, the intensity of the reflected light RL of the laser light L increases and an artifact signal is generated from the transducer array 20 due to the reflected light RL ((b) of FIG. 7). In general, the artifact signal is generated over the entire transducer array 20. In this case, the strip-shaped artifact region R1 appears in the photoacoustic image P. Although not illustrated in FIG. 7, as described above, in the case where the acoustic matching member is provided in a contact portion of the probe, the artifact region caused by the absorption of reflected light by the acoustic matching member also appears. In this case, the absorber region also appears according to the distance between the probe 11 and the subject M.

Then, when the probe 11 comes into contact with the subject, the laser light L is propagated through the subject and the detection surface of the transducer array 20 is covered by the subject. Therefore, the amount of laser light which is directly incident on the transducer array 20 is reduced. As a result, no artifact signal is detected and the artifact region R1 disappears from the photoacoustic image P ((c) of FIG. 7). In contrast, a photoacoustic signal is detected from the absorber in the subject. Therefore, the absorber region R2 appears in the photoacoustic image P ((c) of FIG. 7). However, when the determination unit 28 determines that the probe 11 does not come into contact with the subject M, the intensity of the laser light L is low and the photoacoustic signal from the absorber in a deep part of the subject is hardly detected. When the determination unit 28 determines that the probe 11 comes into contact with the subject M, the intensity of the laser light L increases from the first intensity to the second intensity ((d) of FIG. 7). Therefore, a sufficient amount of laser light L can reach the deep part of the subject M. As a result, the photoacoustic signal from the absorber in the deep part of the subject can also be detected and an absorber region R3 of the deep part also appears in the photoacoustic image P.

The determination unit 28 performs the contact determination on the basis of a combination of the appearance and disappearance of the artifact region R1 and the absorber region R2.

For example, during the process of determining a change from the non-contact state to the contact state, when the artifact region R1 is detected, the determination unit 28 can determine that the state between the probe 11 and the subject M has changed from the non-contact state to the contact state. In addition, during the process of determining the change from the non-contact state to the contact state, when the absorber region R2 is detected after the artifact region R1 is detected, the determination unit 28 can determine that the state between the probe 11 and the subject M has changed from the non-contact state to the contact state. As such, the detection of the artifact region R1 which is a criterion for determining the approach of the probe to the subject M is an indispensable factor for determining the contact state. Therefore, for example, in the case where an absorber, such as a metal component, is inadvertently arranged in front of the detection surface of the probe 11, it is possible to prevent the laser light L from being emitted in an unintended direction. In some cases, the artifact region R1 and the absorber region R2 are detected at the same time according to the repetition period of the laser light L and the approach of the probe 11 to the subject M.

During the process of determining a change from the contact state to the non-contact state, when the artifact region is detected in the photoacoustic image P, the determination unit 28 can determine that the state between the probe 11 and the subject M has changed from the contact state to the non-contact state. According to this determination, it is possible to detect the separation of the probe 11 from the subject M in an early stage. This is because the appearance of the artifact region R1 is earlier than the disappearance of the absorber region R2 in the change from the contact state to the non-contact state.

As described above, the photoacoustic measurement device according to this embodiment has the determination unit that performs contact determination on the basis of the status of a change in a plurality of photoacoustic signals detected by a plurality of acoustic wave detection elements. Therefore, the same effect as that in the first embodiment is obtained.

The photoacoustic measurement method and the probe contact determination method according to this embodiment perform contact determination on the basis of the status of a change in a plurality of photoacoustic signals detected by a plurality of acoustic wave detection elements. Therefore, the same effect as that in the first embodiment is obtained.

Third Embodiment

Figure 8:
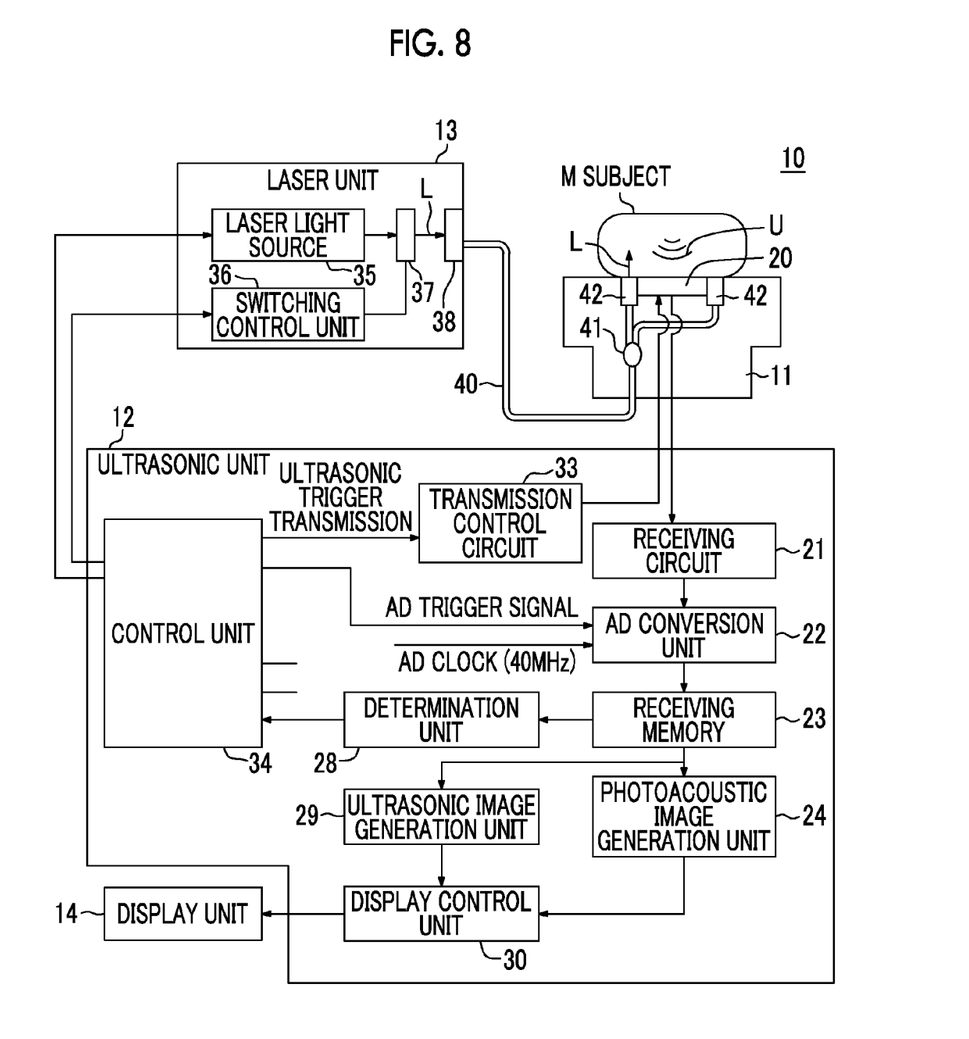
FIG. 8 is a conceptual diagram illustrating the structure of a photoacoustic measurement device according to a third embodiment.

Next, a third embodiment of the photoacoustic measurement device, the photoacoustic measurement method, and the probe contact determination method according to the invention will be described. FIG. 8 is a conceptual diagram illustrating the structure of the photoacoustic measurement device according to the third embodiment. This embodiment differs from the first embodiment in that an ultrasonic image as a reflected acoustic wave image is generated in addition to a photoacoustic image. Therefore, the detailed description of the same components as those in the first embodiment will not be repeated if not particularly necessary.

A photoacoustic measurement device 10 according to this embodiment includes an ultrasonic probe (probe) 11, an ultrasonic unit 12, a laser unit 13, and a display unit 14, similarly to the first embodiment.

<Ultrasonic Unit>

The ultrasonic unit 12 according to this embodiment includes an ultrasonic image generation unit 29 and a transmission control circuit 33 in addition to the structure of the photoacoustic measurement device illustrated in FIG. 1.

In this embodiment, the probe 11 performs the output (transmission) of ultrasonic waves to a subject and the detection (reception) of ultrasonic waves (reflected acoustic waves) which are reflected ultrasonic waves of the ultrasonic waves transmitted to the subject, in addition to the detection of a photoacoustic signal. An ultrasonic transducer which transmits and receives ultrasonic waves may be the ultrasonic transducer according to the invention or a new ultrasonic transducer which is separately provided in the probe 11 in order to transmit and receive ultrasonic waves. In addition, the transmission and reception of the ultrasonic waves may be separated from each other. For example, ultrasonic waves may be transmitted from a position different from the position of the probe 11 and the probe 11 may receive the reflected ultrasonic waves of the transmitted ultrasonic waves.

A control unit 34 transmits an ultrasonic transmission trigger signal for instructing the transmission control circuit 33 to transmit ultrasonic waves when an ultrasonic image is generated. When receiving the trigger signal, the transmission control circuit 33 directs the probe 11 to transmit ultrasonic waves. After transmitting the ultrasonic waves, the probe 11 detects ultrasonic waves reflected from the subject.

The reflected ultrasonic waves detected by the probe 11 are input to an AD conversion unit 22 through a receiving circuit 21. The control unit 34 transmits a sampling trigger signal to the AD conversion unit 22 in synchronization with the transmission of the ultrasonic waves and directs the AD conversion unit 22 to sample the reflected ultrasonic waves. The AD conversion unit 22 stores the sampled signal of the reflected ultrasonic waves in the receiving memory 23. The order of the sampling of the photoacoustic signal and the sampling of the reflected ultrasonic waves is not particularly limited.

The ultrasonic image generation unit 29 performs signal processing, such as a reconstruction process, a detection process, and a logarithmic conversion process, on the basis of the reflected ultrasonic waves (the sampled signal thereof) detected by a plurality of ultrasonic transducers of the probe 11 to generate ultrasonic image data. The image data can be generated by, for example, the delay and sum method, similarly to the generation of the image data by the photoacoustic image generation unit 24.

For example, a display control unit 30 separately displays the photoacoustic image and the ultrasonic image on a display unit 14 or displays a composite image thereof on the display unit 14. For example, the display control unit 30 superimposes the photoacoustic image and the ultrasonic image to perform image composition.

In this embodiment, the photoacoustic measurement device generates the ultrasonic image in addition to the photoacoustic image. Therefore, it is possible to obtain the effect of observing a part which is not capable of being imaged in the photoacoustic image, by referring to the ultrasonic image, in addition to the effect of the first embodiment.

What is claimed is:

1. A photoacoustic measurement device comprising:
   a probe having a light emitting unit that emits measurement light and a plurality of acoustic wave detection elements that measure a photoacoustic signal from a subject which is caused by the emission of the measurement light;
   a processor configured to determine whether a state between the probe and the subject is a touch state or a non-touch state; and
   a light intensity control unit that controls the intensity of the measurement light such that the measurement light has a first intensity when the processor determines that the state between the probe and the subject is the non-touch state and controls the intensity of the measurement light such that the measurement light has a second intensity higher than the first intensity when the processor determines that the state between the probe and the subject is the touch state,
   wherein the processor performs the determination on the basis of a status of a change in a plurality of photoacoustic signals detected by the plurality of acoustic wave detection elements,
   wherein the processor calculates the number of acoustic wave detection elements which detect the plurality of photoacoustic signals on the basis of the plurality of photoacoustic signals, decides a change in the number of acoustic wave detection elements as the change in the plurality of photoacoustic signals, compares the number of acoustic wave detection elements which detect the plurality of photoacoustic signals with a threshold number of acoustic wave detection elements, and performs the determination on the basis of the comparison result, and
   wherein the threshold number of acoustic wave detection elements which detect the plurality of photoacoustic signals when a change from the touch state to the non-touch state is determined is less than the threshold number of acoustic wave detection elements when a change from the non-touch state to the touch state is determined.

2. The photoacoustic measurement device according to claim 1,
   wherein the threshold number of acoustic wave detection elements which detect the plurality of photoacoustic signals when a change from the touch state to the non-touch state is determined is equal to the threshold number of acoustic wave detection elements when a change from the non-touch state to the touch state is determined.

3. The photoacoustic measurement device according to claim 1,
   wherein the processor counts the number of only a part of the plurality of acoustic wave detection elements which detect the plurality of photoacoustic signals.

4. The photoacoustic measurement device according to claim 1,
   wherein the processor detects the appearance or disappearance of an absorber region indicating an absorber in the subject and an artifact region indicating an artifact caused by the emission of the measurement light in a photoacoustic image which is generated on the basis of the plurality of photoacoustic signals, determines the appearance or disappearance of the absorber region and the artifact region as the change in the plurality of photoacoustic signals, and performs the determination on the basis of a combination of the appearance and disappearance of the absorber region and the artifact region.

5. The photoacoustic measurement device according to claim 4,
   wherein, during the determination of the change from the touch state to the non-touch state, when the artifact region is detected in the photoacoustic image, the processor determines that the state between the probe and the subject has changed from the touch state to the non-touch state.

6. The photoacoustic measurement device according to claim 4,
   wherein, during the determination of the change from the non-touch state to the touch state, when the artifact region is detected in the photoacoustic image and the absorber region is detected after the artifact region is detected, the processor determines that the state between the probe and the subject has changed from the non-touch state to the touch state.

7. A photoacoustic measurement method comprising:
   using the photoacoustic measurement device according to claim 1;
   emitting measurement light and detecting the plurality of photoacoustic signals by using the probe having the light emitting unit that emits measurement light and the plurality of acoustic wave detection elements;
   determining whether a state between the probe and the subject is the touch state or the non-touch state on the basis of the status of a change in the plurality of photoacoustic signals detected by the plurality of acoustic wave detection elements;
   controlling the intensity of the measurement light such that the measurement light has the first intensity when it is determined that the state between the probe and the subject is the non-touch state and controlling the intensity of the measurement light such that the measurement light has the second intensity higher than the first intensity when it is determined that the state between the probe and the subject is the touch state, thereby measuring the photoacoustic signals from the subject.

8. The photoacoustic measurement method according to claim 7,
wherein the number of acoustic wave detection elements which detect the plurality of photoacoustic signals is calculated on the basis of the plurality of photoacoustic signals,
a change in the number of acoustic wave detection elements is decided as the change in the plurality of photoacoustic signals,
the number of acoustic wave detection elements which detect the plurality of photoacoustic signals is compared with a threshold number of acoustic wave detection elements, and
the determination is performed on the basis of the comparison result.

9. The photoacoustic measurement method according to claim 8,
wherein the threshold number of acoustic wave detection elements which detect the plurality of photoacoustic signals when a change from the touch state to the non-touch state is determined is less than the threshold number of acoustic wave detection elements when a change from the non-touch state to the touch state is determined.

10. The photoacoustic measurement method according to claim 8,
wherein the number of only specific acoustic wave detection elements among the plurality of acoustic wave detection elements is counted.

11. The photoacoustic measurement method according to claim 7,
wherein the appearance or disappearance of an absorber region indicating an absorber in the subject and an artifact region indicating an artifact caused by the emission of the measurement light is detected in a photoacoustic image which is generated on the basis of the plurality of photoacoustic signals,
the appearance or disappearance of the absorber region and the artifact region is determined as the change in the plurality of photoacoustic signals, and
the determination is performed on the basis of a combination of the appearance and disappearance of the absorber region and the artifact region.

12. The photoacoustic measurement method according to claim 11,
wherein, during the determination of the change from the touch state to the non-touch state, when the artifact region is detected in the photoacoustic image, it is determined that the state between the probe and the subject has changed from the touch state to the non-touch state.

13. The photoacoustic measurement method according to claim 11,
wherein, during the determination of the change from the non-touch state to the touch state, when the artifact region is detected in the photoacoustic image and the absorber region is detected after the artifact region is detected, it is determined that the state between the probe and the subject has changed from the non-touch state to the touch state.

14. A probe contact determination method comprising:
emitting measurement light and detecting the plurality of photoacoustic signals by using the photoacoustic measurement device according to claim 1;
using the probe having the light emitting unit that emits measurement light and the plurality of acoustic wave detection elements; and
determining whether a state between the probe and the subject is the touch state or the non-touch state on the basis of the status of a change in the plurality of photoacoustic signals detected by the plurality of acoustic wave detection elements.

15. The probe contact determination method according to claim 14,
wherein the number of acoustic wave detection elements which detect the plurality of photoacoustic signals is calculated on the basis of the plurality of photoacoustic signals,
a change in the number of acoustic wave detection elements is decided as the change in the plurality of photoacoustic signals,
the number of acoustic wave detection elements which detect the plurality of photoacoustic signals is compared with a threshold number of acoustic wave detection elements, and
the determination is performed on the basis of the comparison result.

16. The probe contact determination method according to claim 14,
wherein the appearance or disappearance of an absorber region indicating an absorber in the subject and an artifact region indicating an artifact caused by the emission of the measurement light is detected in a photoacoustic image which is generated on the basis of the plurality of photoacoustic signals,
the appearance or disappearance of the absorber region and the artifact region is determined as the change in the plurality of photoacoustic signals, and
the determination is performed on the basis of a combination of the appearance and disappearance of the absorber region and the artifact region.

17. The probe contact determination method according to claim 16,
wherein, during the determination of the change from the touch state to the non-touch state, when the artifact region is detected in the photoacoustic image, it is determined that the state between the probe and the subject has changed from the touch state to the non-touch state.

* * * * *